(12) United States Patent
Taniike et al.

(10) Patent No.: US 6,878,262 B2
(45) Date of Patent: Apr. 12, 2005

(54) ANALYTICAL ELEMENT AND MEASURING DEVICE AND SUBSTRATE QUANTIFICATION METHOD USING THE SAME

(75) Inventors: Yuko Taniike, Osaka (JP); Shin Ikeda, Katano (JP); Shiro Nankai, Hirakata (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 331 days.

(21) Appl. No.: 10/216,716

(22) Filed: Aug. 13, 2002

(65) Prior Publication Data

US 2003/0003524 A1 Jan. 2, 2003

Related U.S. Application Data

(63) Continuation of application No. PCT/JP01/10866, filed on Dec. 11, 2001.

(30) Foreign Application Priority Data

Dec. 13, 2000 (JP) ........................................ 2000-378323

(51) Int. Cl.$^7$ .......................... G01N 27/327; A61B 5/05
(52) U.S. Cl. .............................. 205/777.5; 204/403.14; 600/345; 600/347
(58) Field of Search ...................... 205/777.5; 606/181; 600/345–347; 204/403.01, 403.02, 403.14

(56) References Cited

U.S. PATENT DOCUMENTS 5,714,123 A 2/1998 Sohrab
6,488,828 B1 * 12/2002 Bhullar et al. .......... 204/403.01
6,699,382 B2 * 3/2004 Yoshioka et al. ........ 205/777.5

FOREIGN PATENT DOCUMENTS

| CN | 1186243 A | 7/1998 | |
|---|---|---|---|
| EP | 0 964 060 A2 | 12/1999 | |
| EP | 0 964 245 A2 | 12/1999 | |
| JP | 61-115964 | 7/1986 | |
| JP | 3-202764 | 9/1991 | |
| JP | 3-237349 | 10/1991 | |
| JP | 04-194660 A | 7/1992 | |
| JP | 6-213843 | 8/1994 | |
| JP | 07-159366 A * | 6/1995 | .......... G01N/27/28 |
| JP | 2517153 | 4/1996 | |
| JP | 8-145938 | 6/1996 | |
| JP | 9-184818 | 7/1997 | |
| JP | 09-285459 | 11/1997 | |
| JP | 10-28683 | 2/1998 | |
| JP | 2000-231 | 1/2000 | |
| JP | 2000-217804 | 8/2000 | |
| JP | 2000-232973 | 8/2000 | |

OTHER PUBLICATIONS

JPO computer translation of Satoshi et al. (JP 07–159366).*
JPO computer translation of Tadahisa (JP 09–285459).*

* cited by examiner

Primary Examiner—Alex Noguerola
(74) Attorney, Agent, or Firm—McDermott Will & Emery LLP (57) ABSTRACT

The present invention provides an analytical element which is free from evaporation of a sample during measurement and therefore capable of quantifying a substrate using a very small amount of sample with high accuracy and which is free from scattering of the sample during and after the measurement and therefore hygienically excellent; and a measuring device and a substrate quantification method using the same. The analytical element comprises a cavity for accommodating a sample, a working electrode and a counter electrode exposed to an inside of the cavity, a reagent layer which comprises at least an oxidoreductase and is formed inside or in the vicinity of the cavity, an opening communicating with the cavity and a member covering the opening.

20 Claims, 9 Drawing Sheets

ANALYTICAL ELEMENT AND MEASURING DEVICE AND SUBSTRATE QUANTIFICATION METHOD USING THE SAME

This application is a continuation of PCT/JP01/10866 Dec. 11, 2001.

TECHNICAL FIELD

The present invention relates to a method for rapid and highly accurate quantification of a substrate contained in a sample and to an analytical element and a measuring device used therein.

BACKGROUND ART

Methods using polarimetry, colorimetry, reductimetry and a variety of chromatographies have been developed as methods for quantitative analysis of sugars such as sucrose and glucose. These methods, however, are all poorly specific to sugars and hence have poor accuracy. Among these methods, the polarimetry is simple in manipulation, but is largely affected by the temperature during the manipulation. Therefore, the polarimetry is not suitable as a method for simple quantification of sugars at home, etc. for ordinary people.

Recently, various types of biosensors utilizing the specific catalytic action of enzymes have been under development.

The following will describe a method of glucose quantification as one example of the method of quantifying a substrate contained in a sample. As an electrochemical method of glucose quantification, a method using glucose oxidase (EC 1.1.3.4: hereinafter abbreviated to GOD) and an oxygen electrode or a hydrogen peroxide electrode is generally well-known (see "Biosensor" ed. by Shuichi Suzuki, Kodansha, for example).

GOD selectively oxidizes β-D-glucose as a substrate to D-glucono-δ-lactone using oxygen as an electron mediator. In the presence of oxygen, oxygen is reduced to hydrogen peroxide during the oxidation reaction process by GOD. The decreased amount of oxygen is measured by the oxygen electrode, or the increased amount of hydrogen peroxide is measured by the hydrogen peroxide electrode. Since the decreased amount of oxygen and the increased amount of hydrogen peroxide are proportional to the content of glucose in the sample, glucose quantification is possible based on the decreased amount of oxygen or the increased amount of hydrogen peroxide.

The above method utilizes the specificity of the enzyme reaction to enable accurate quantification of glucose in the sample. However, as speculated from the reaction process, there is a drawback that the measurement results are largely affected by the oxygen concentration of the sample, and if the oxygen is absent in the sample, the measurement is infeasible.

Under such circumstances, glucose sensors of new type have been developed which use as the electron mediator potassium ferricyanide, an organic compound or a metal complex such as a ferrocene derivative and a quinone derivative without using oxygen as the electron mediator. In the sensors of this type, reduced form electron mediator resulting from the enzyme reaction is oxidized on a working electrode, and the concentration of glucose contained in the sample can be determined based on the amount of this oxidation current. At this time, on a counter electrode, a reaction in which oxidized form electron mediator is reduced to produce reduced form electron mediator proceeds. With the use of such an organic compound or metal complex as the electron mediator in place of oxygen, it is possible to form a reagent layer while a known amount of GOD and the electron mediator are carried in a stable state and a precise manner on the electrode, so that accurate quantification of glucose is possible without being affected by the oxygen concentration of the sample. In this case, it is also possible to integrate the reagent layer, in an almost dry state, with an electrode system, and hence disposable glucose sensors based on this technique have recently been receiving a lot of attention. A typical example thereof is a biosensor disclosed in Japanese Patent Publication No. 2517153. In such a disposable glucose sensor, it is possible to measure glucose concentration easily with a measurement device by simply introducing a sample into the sensor connected detachably to the measurement device. The application of such a technique is not limited to quantification of glucose and may be extended to quantification of any other substrate contained in the sample.

In the above-mentioned conventional biosensors, even after introduction of the sample into the biosensor, part of the sample is exposed to outside, and part of the sample therefore evaporates during the measurement, possibly causing a change in substrate concentration of the sample. Although the conventional biosensors are capable of measuring a sample in the order of microliter, development of biosensors capable of measuring a sample in a further smaller amount has been anxiously hoped for from various fields in recent years. However, with the reduction of the sample, even a slight change in substrate concentration may cause variations in measured values in the conventional biosensors.

Therefore, an object of the present invention is to provide an analytical element which can prevent evaporation of a sample during measurement and therefore quantify a substrate using a very small amount of sample with high accuracy and which can prevent scattering of the sample during and after the measurement and is therefore hygienically excellent.

Another object of the present invention is to provide a measuring device comprising such an analytical element and a method of substrate quantification.

DISCLOSURE OF INVENTION

An analytical element in accordance with the present invention is characterized by comprising a cavity for accommodating a sample, a working electrode and a counter electrode exposed to an inside of the cavity, a reagent layer which comprises at least an oxidoreductase and is formed inside or in the vicinity of the cavity, an opening communicating with the cavity and a member covering the opening.

Also, a measuring device in accordance with the present invention comprises a combination of the above-described analytical element with voltage application means for applying a voltage between the working electrode and the counter electrode and signal detecting means for detecting an electric signal between the working electrode and the counter electrode upon voltage application, and the amount of reaction between a substrate contained in the sample and the oxidoreductase is electrochemically detected to quantify the substrate.

A substrate quantification method in accordance with the present invention comprises the steps of: preparing the above-described analytical element; supplying the sample to the analytical element to react a substrate contained in the sample with the oxidoreductase; closing the opening; applying a voltage between the working electrode and the counter electrode; and detecting a change in electric signal between the working electrode and the counter electrode upon the voltage application.

BEST MODE FOR CARRYING OUT THE INVENTION

An analytical element in accordance with the present invention comprises a cavity for accommodating a sample, a working electrode and a counter electrode exposed to an inside of the cavity, a reagent layer which comprises at least an oxidoreductase and is formed inside or in the vicinity of the cavity, an opening communicating with the cavity and a member covering the opening. In this analytical element, since the opening can be closed by the member covering the opening after introduction of the sample, the sample inside the cavity is not exposed to the air outside, and it is therefore possible to prevent evaporation of the sample. This particularly leads to an improvement in the measuring accuracy of measurements using a very small amount of sample. Further, this also prevents scattering of the sample to outside during and after the measurement, and it is therefore possible to provide an analytical element which is hygienically excellent even with the use of an infectious sample such as blood in particular. The member covering the opening, when integrated with the analytical element, ensures interception from outside.

The member covering the opening may be one covering at least a part of the opening communicating with the cavity for accommodating the sample, but it is preferred to cover the whole opening.

In a preferred analytical element of the present invention, an element body comprising an insulating member is provided with a cavity for accommodating a sample and a working electrode and a counter electrode exposed to the inside of the cavity. One end of the cavity serves as a sample supply port while the other end serves as an air vent, and the sample is introduced from the sample supply port into the cavity by capillary action. The member covering the opening of the cavity substantially closes both of the sample supply port and the air vent. In another preferred embodiment, the cavity comprises a depression formed in the element body and a sample supply port and an air vent communicating with the depression. In this embodiment, in order to cause enzyme reaction to take place in the depression, the member covering the opening of the cavity may be one covering merely the inlet side of the depression.

The material of the member covering the opening may be any material having a property allowing interception of the outside air so as to suppress evaporation of the sample. Such examples include thermoplastic resins such as polyethylene, polystyrene, poly vinyl chloride, polyamide and saturated polyester resin, thermosetting resins such as urea resin, melamine resin, phenol resin, epoxy resin and unsaturated polyester resin, metal such as stainless steel, silver and platinum, or carbon.

The shape of the member covering the opening is subject to no particular limitation and may be any shape appropriate for the shape of the opening. The member covering the opening is preferably a puncture member. This makes it possible to take a sample and measure the sample with the use of just one element, to ensure the use of the sample that has been taken for measurement, and to shorten the time required for taking and measuring the sample. This also makes it possible to downsize the constitution of the analytical element and further reduce the amount of sample necessary for the measurement. Furthermore, this enables reduction in the number of components and the number of manufacturing steps.

Also, the member covering the opening is preferably transparent. This makes it possible to easily check whether the sample is duly supplied into the analytical element by visual observation. The member covering the opening may also be opaque, and this produces the effect of lessening the fear of a subject particularly in measurements using blood since the sample is invisible from outside.

In the above, the member covering the opening is preferably configured so as to slide on the analytical element body. This allows the subject to manipulate easily.

The member covering the opening may be provided with the working electrode or the counter electrode. This makes it possible to downsize the constitution of the analytical element and further reduce the amount of sample necessary for the measurement.

The member covering the opening may be provided with the reagent layer. This allows a plurality of reagents to be readily carried while separated from one another within the analytical element; therefore, this realizes high performance and particularly improves the storage stability of the analytical element.

An analytical element in accordance with a preferred embodiment of the present invention comprises: a rod-like element body comprising an insulating member which has a depression for accommodating a sample at its side face in the vicinity of its tip end and a working electrode and a counter electrode arranged so as to be exposed to an inside of the depression; a cover which covers the face of the element body having the depression, the cover having a groove along a longitudinal direction of the element body at a portion facing the depression; and a puncture member which moves in the longitudinal direction of the element body in the groove and sticks out of the tip end of the element body to puncture a subject. A sample supply opening communicating with the depression is formed between the tip end of the element body and the cover. An air vent is formed at or above a position of the cover corresponding to the depression. The puncture member is preferably capable of substantially covering the depression.

Herein, the puncture member may also serve as the working electrode or the counter electrode. In this case, the element body may be provided with the counter electrode or the working electrode.

Another preferred analytical element in accordance with the present invention comprises: an element body comprising an insulating base plate on which an electrode system comprising a working electrode and a counter electrode is formed and a cover member which covers the base plate and forms a sample supply pathway communicating with the electrode system between the cover and the base plate; and a top cover. The sample supply pathway extends from a sample supply port at one end of the element body to an air vent formed in the cover member. The top cover is combined to the element body by sliding it in a direction perpendicular to the element body such that it closes the sample supply port and the air vent when it is in close contact with the element body. The working electrode and/or the counter electrode may be provided with the cover member side. The reagent layer is formed on the base plate and/or the cover member so as to be exposed to the sample supply pathway.

A measuring device in accordance with the present invention comprises the combination of the above-describe analytical element with voltage application means for applying a voltage between the working electrode and the counter electrode of the analytical element and signal detecting means for detecting an electric signal between the working electrode and the counter electrode upon voltage application, wherein the amount of reaction between a substrate contained in the sample and the oxidoreductase carried on the analytical element is electrochemically detected to quantify the substrate.

A constitution that the analytical element is separated from the member covering the opening enables reduction in manufacturing cost of the analytical element.

Herein, the member covering the opening is preferably detachable from the analytical element body. This allows only the member covering the opening to be cleaned and makes it possible to provide a measuring device which is hygienically excellent.

Another preferred measuring device in accordance with the present invention comprises: an element body comprising an insulating base plate on which an electrode system comprising a working electrode and a counter electrode is formed and a cover member which covers the base plate and forms a sample supply pathway communicating with the electrode system between the cover and the base plate; and a cylindrical outer cover for fixing the element body therein. The sample supply pathway of the element body extends from a sample supply port at the tip end of the element body to an air vent formed in the cover member. The outer cover has an air vent communicating with the above-described air vent. The measuring device comprises: an air vent allowing the air vent of the outer cover to communicate with the air vent of the element body; an inner cover capable of sliding in a longitudinal direction of the outer cover between the outer cover and the element body; a puncture member which sticks out of the inside of the outer cover toward a subject; voltage application means for applying a voltage between the working electrode and the counter electrode of the analytical element; and signal detecting means for detecting an electric signal between the working electrode and the counter electrode upon voltage application.

The measuring device further comprises needle driving means for driving the puncture member, needle position controlling means for controlling needle position, inner cover driving means for driving the inner cover, and inner cover position controlling means for controlling inner cover position. The inner cover is, until a sample is taken, at a position at which the sample supply port and the air vent of the element body are open. After the sample is taken from the sample supply port, the inner cover moves inside the outer cover toward its tip end to block the air vent of the outer cover and the air vent of the element body, and the front end portion of the inner cover bends to close the sample supply port. These operations of the inner cover are carried out by the driving means on the basis of the signal from the position controlling means.

A substrate quantification method in accordance with the present invention comprises the steps of: preparing the above-described analytical element; supplying the sample to the analytical element to react a substrate contained in the sample with the oxidoreductase of the analytical element; closing the opening of the analytical element; applying a voltage between the working electrode and the counter electrode; and detecting a change in electric signal between the working electrode and the counter electrode upon the voltage application.

The voltage is generally applied between the working electrode and the counter electrode so as to make the working electrode positive. This oxidizes the reduced form electron mediator resulting from the enzyme reaction on the working electrode. The change of electric signal between the working electrode and the counter electrode is detected as the amount of this oxidation current of the electron mediator. On the basis of this amount of current, the substrate concentration of the sample can be obtained. Instead of the measured value of this current, the value obtained by converting the current into voltage may be displayed.

According to the present invention, since the sample inside the cavity of the analytical element is not exposed to the outside air, evaporation of the sample is prevented and the measuring accuracy is improved particularly in the case of measurements using a very small amount of sample. Further, since the sample is prevented from scattering to outside during and after the measurement, it is hygienically excellent even with the use of an infectious sample such as blood in particular.

As the working electrode used for the analytical element of the present invention, a conductive material which is not subject to oxidation upon oxidation of the electron mediator is used. As the counter electrode, a commonly used conductive material such as palladium, gold, platinum or carbon may be used. The surface of an electrically insulating material may be coated with such a conductive material.

As the oxidorecuctase, one adequate for the substrate contained in the sample to be measured may be used. Such examples include fructose dehydrogenase, glucose oxidase, glucose dehydrogenase, alcohol oxidase, lactate oxidase, cholesterol oxidase, xanthine oxidase, amino acid oxidase, etc.

The puncture member may be any member having enough strength for puncture, and such examples include a needle composed of metal, such as stainless steel, gold or platinum, or carbon. When the puncture member is used as the working electrode or counter electrode, a conductive material such as gold, platinum or carbon may be used, or the surface of an insulating material may be coated with such a conductive material.

The analytical element of the present invention is designed for measuring samples which are solutions containing various kinds of substrates and body fluids of which sampling amount is required to be reduced further. Examples of the body fluids include whole blood, plasma, serum, interstitial fluid and saliva. These examples are not to be construed as limiting the samples to be measured by the present invention.

In the following, the present invention will be described in detail with reference to drawings illustrating examples thereof. Since structural drawings are used hereinafter for facilitating understanding, they are not necessarily accurate as to relative size and positional relationship of each element. The following examples will describe analytical elements, measuring devices and quantification methods used for glucose quantification, but the substrate is not limited to glucose.

EXAMPLE 1

Figures 1, 2:
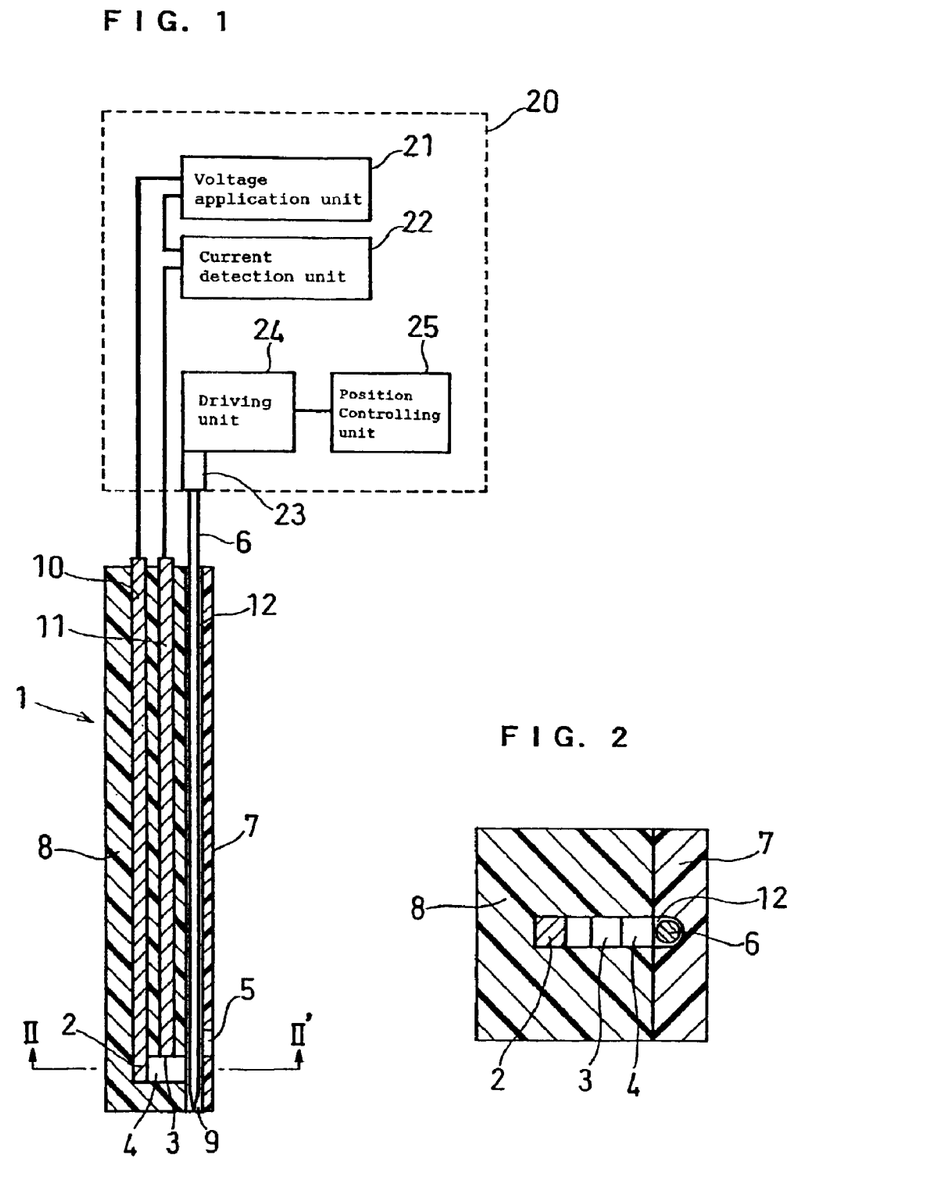
FIG. 1 is a schematic view showing the constitution of a measuring device in accordance with one embodiment of the present invention.
FIG. 2 is an enlarged view of section II–II" of FIG. 1.
Figure 3:
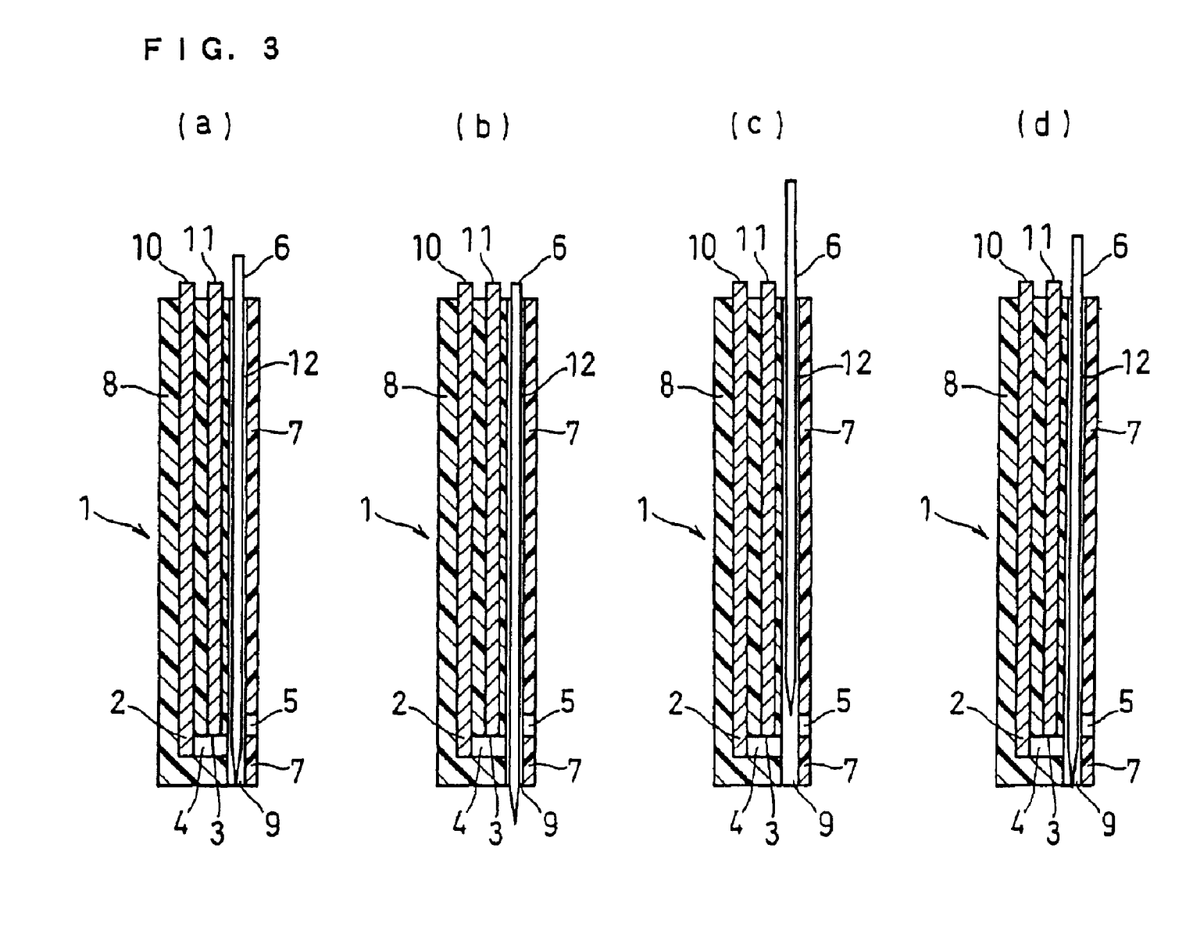
FIG. 3 is longitudinal cross-sectional views showing the operation of a puncture member of an analytical element in accordance with one embodiment of the present invention.
Figure 4:
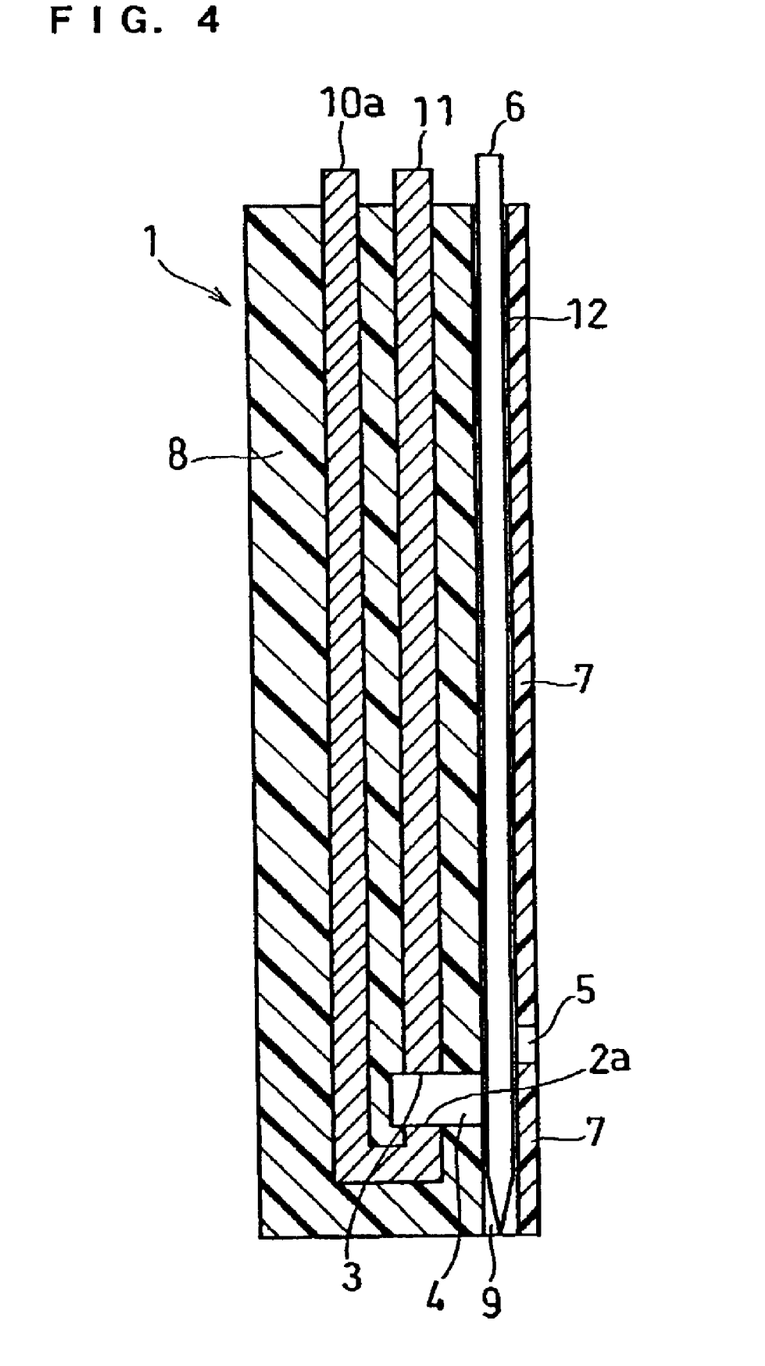
FIG. 4 is a longitudinal cross-sectional view of an analytical element in accordance with another embodiment of the present invention from which the reagent layer and surfactant layer are omitted.
Figure 5:
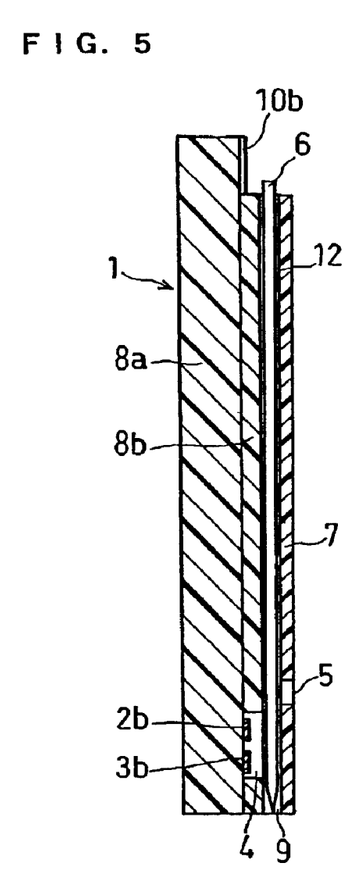
FIG. 5 is a longitudinal cross-sectional view of an analytical element in accordance with still another embodiment of the present invention from which the reagent layer and surfactant layer are omitted.

FIG. 1 is a schematic view of a measuring device used in this example and is a longitudinal cross-sectional view of an analytical element from which the reagent layer and surfactant layer are omitted. FIG. 3 is a longitudinal cross-sectional view showing the operation of a puncture member in the analytical element, and, FIGS. 4 to 5 are longitudinal cross-sectional views showing other forms of electrodes in the analytical element of this example from which the regent layer and surfactant layer are omitted.

The measuring device as shown in FIG. 1 is composed of an analytical element 1 and a main body 20. The analytical element 1 is composed of a puncture member 6, a rod-like member 8 and a cover 7. The rod-like member 8 comprises a cavity 4 for accommodating a sample, a working electrode 2 and a counter electrode 3 exposed to the inside of the cavity 4, and a reagent layer (not shown in the figure) carried inside the cavity 4. The cover 7 is joined to the rod-like member 8 so as to cover its cavity 4 side and has a groove 12 for guiding the puncture member 6 and an air vent 5 that is open in the vicinity of the cavity 4. The groove 12 has, at its lower part, an opening which serves as a sample supply port 9 from which the sample is introduced into the cavity 4 by capillary action. The opening of the cavity 4 is substantially closed by the puncture member 6 in a state as shown in FIG. 1.

A working electrode lead 10 composed of a 30 mm long conductive material and a counter electrode lead 11 composed of a 29 mm long conductive material are embedded in the rod-like member 8 by insert-molding a synthetic resin which is electrically insulating. A section of these conductive members is a rectangle of 0.5 mm×1 mm. The tip ends of the leads 10 and 11 exposed to the inside of the cavity 4 serve as the working electrode 2 and the counter electrode 3, respectively. The cavity 4 has a size of 1 mm×1 mm×1 mm. The puncture member 6 is a column having a diameter of 1.0 mm and a length of 40 mm.

An aqueous solution containing GOD as an oxidoreductase and potassium ferricyanide as an electron mediator is dropped into the cavity 4 and is then dried to form a reagent layer. Further, for the purpose of facilitating smooth supply of the sample, a surfactant layer containing lecithin as a surfactant is formed over the reagent layer and from the cavity 4 up to the sample supply port 9.

The cover 7 is bonded to the rod-like member 8, on which the reagent layer and the surfactant layer are formed in the above manner, in such a manner as to accommodate the puncture member 6 therein to fabricate the analytical element 1.

The main body 20 comprises a voltage application unit 21 for applying a constant voltage between the working electrode 2 and the counter electrode 3 of the analytical element 1, a current detection unit 22 for detecting a current flowing between the working electrode 2 and the counter electrode 3, a driving unit 24 for driving the puncture member 6 vertically, and a position controlling unit 25 for controlling the position of the puncture member 6. The puncture member 6 is connected via a holder 23 to the driving unit 24. The working electrode lead 10 and the counter electrode lead 11 are connected to the voltage application unit 21 and the current detection unit 22, respectively.

Using the above-described measuring device of this example, the concentration of β-D-glucose in sample solutions was quantified. First, several kinds of sample solutions having different β-D-glucose concentrations were prepared. Using the position controlling unit 25 and the driving unit 24, the puncture member 6 was moved to a position at which it did not close the air vent 5 and the sample supply port 9 as shown in FIG. 3(c), and a sample solution was then brought in contact with the sample supply port 9. Since the air vent 5 communicated with the cavity 4, the sample solution introduced to the sample supply port 9 was permeated by capillary action and supplied into the cavity 4. Thereafter, while the puncture member 6 was held at the position as shown in FIG. 3(c) or after the puncture member 6 was moved to a position at which it closed the air vent 5 and the sample supply port 9 as shown in FIG. 3(d), a voltage of 500 mV was applied to the working electrode 2 with respect to the counter electrode 3 by the voltage application unit 21. The value of the current flowing through the working electrode 2 was then measured by the current detection unit 22. Measurements were performed when the humidity upon measurement was 30% and 100%, and the measurement results were compared.

When the position of the puncture member 6 was held as shown in FIG. 3(d), the current response observed was proportional to the glucose concentration of the sample solution at either humidity. In the case of the measurements performed under the environment of a humidity of 100%, evaporation of the sample inside the cavity 4 does not occur; thus, even when the air vent 5 and the sample supply port 9 were not closed by the puncture member 6 as shown in FIG. 3(c), the response obtained was equivalent to that obtained when the position of the puncture member 6 was as shown in FIG. 3(d). However, in the case of the measurements performed under the environment of a humidity of 30%, the response obtained was one which shifted from the measurement value obtained at the humidity of 100% toward the positive side when the position of the puncture member 6 was held as shown in FIG. 3(c). On the other hand, when the position of the puncture member 6 was as shown in FIG. 3(d), the response obtained was in good agreement with the measurement value obtained at the humidity of 100%. This is presumably because the puncture member 6 was able to suppress the evaporation of the sample solution inside the sample supply section 4 during the measurement.

The following will describe a method of measuring the concentration of a substrate in a biological component using the measuring device of this example. First, the puncture member 6 is set at the position as shown in FIG. 3(a), and the analytical element 1 is then pressed against a subject such that the sample supply port 9 comes in contact with the skin. Next, as shown in FIG. 3(b), the skin of the subject is punctured by the puncture member 6. This causes a body fluid to leak from the skin. Thereafter, as shown in FIG. 3(c), the puncture member 6 is moved to a position at which the air vent 5 is open, and is fixed at the position; this causes the body fluid to be introduced into the sample supply section 4. After a lapse of certain time from the puncture, as shown in FIG. 3(d), the puncture member 6 is moved to a position at which the puncture member 6 closes the air vent 5 and the sample supply port 9 and its tip end does not stick out of the sample supply port 9 to outside the analytical element 1. Subsequently, a voltage of 500 mV is applied to the working electrode 2 with respect to the counter electrode 3 by the voltage application unit 21, and the value of the current flowing through the working electrode 2 is then detected by the current detection unit 22 to measure the concentration of the substrate in the body fluid.

The layout of the working electrode 2 and the counter electrode 3 is not limited to that as shown in FIG. 1. For example, it may be such a layout as shown in FIG. 4 in which the working electrode 2 and the counter electrode 3 are arranged at opposite sides of the cavity 4. Such a layout allows the current density of the electrode surface to be more uniform, leading to an improvement in measuring sensitivity.

Figure 6:
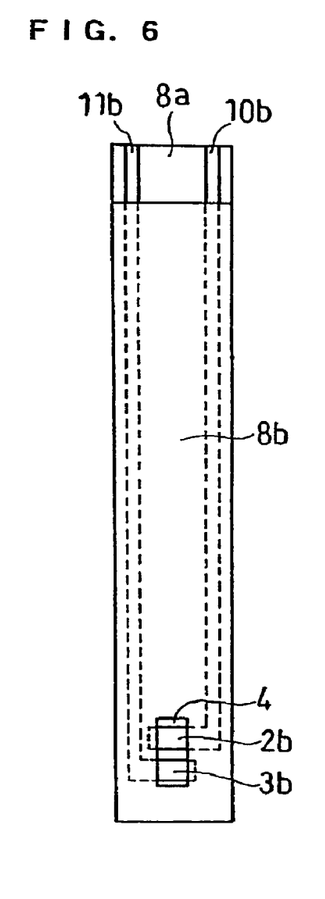
FIG. 6 is a front view of a rod-like member of the same analytical element.

Also, the layout may be as shown in FIG. 5 and FIG. 6 in which the working electrode 2 and the counter electrode 3 are arranged on the same plane. In this case, the above-mentioned rod-like member 8 is formed by combining members 8a and 8b composed of an electrically insulating synthetic resin. The method of producing this analytical element will be explained: first, two pieces of noble metal such as palladium foil, i.e., a working electrode 2b and its lead 10b and a counter electrode 3b and its lead 11b, are attached to the surface of the member 8a. The member 8a having the electrodes and leads formed thereon is combined to the member 8b having a hole for forming the cavity 4. A cover 7 which is the same as that described above is joined to the resultant rod-like member having the electrodes 2b and 3b formed on the same plane, to complete the analytical element.

Instead of the above-mentioned electrodes and leads composed of metal foil, electrodes may be formed by sputtering noble metal such as palladium on the surface of the member 8a to form a conductive layer and trimming the conductive layer by laser so as to substantially separate the working electrode and its lead and the counter electrode and its lead from one another. This enables concurrent formation of the working electrode 2 and the counter electrode 3 and therefore facilitates the manufacturing.

Figure 7:
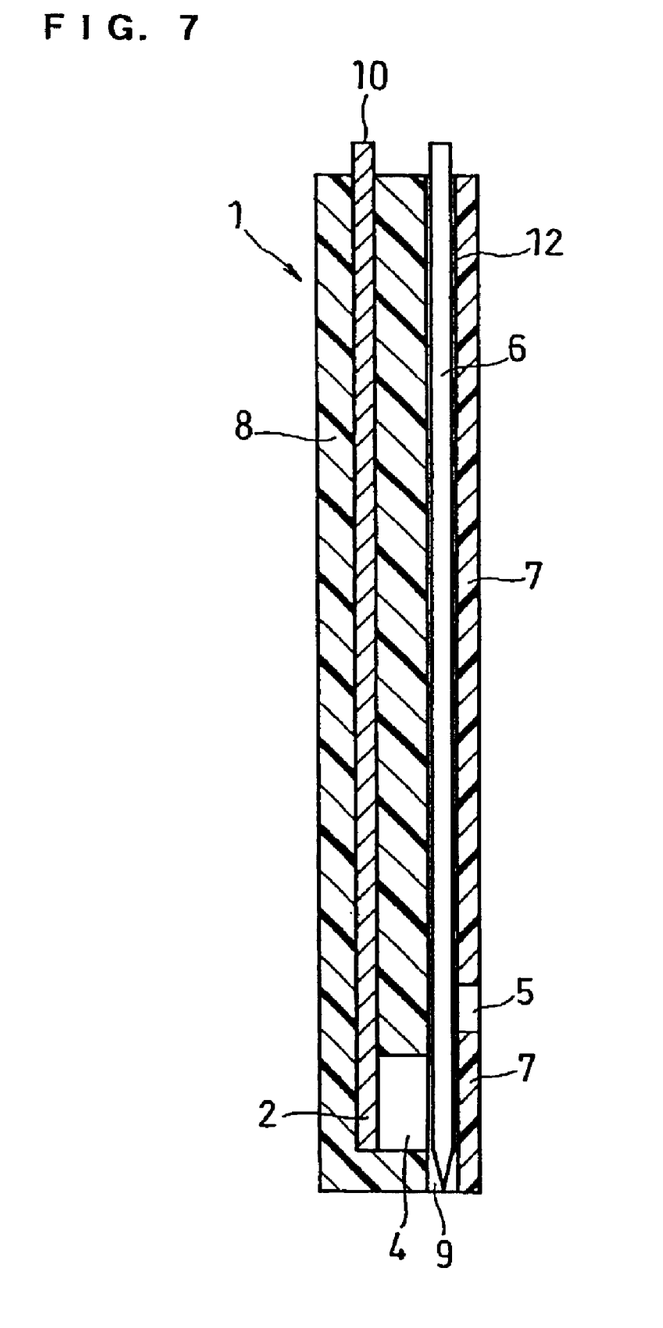
FIG. 7 is a longitudinal cross-sectional view of an analytical element in accordance with still another embodiment of the present invention from which the reagent layer and surfactant layer are omitted.

Further, as shown in FIG. 7, the puncture member 6 composed of a conductive material may also serve as the counter electrode 3. This reduces the number of parts and therefore enables size reduction, so that further reduction is possible in the amount of sample necessary for the measurement.

EXAMPLE 2

Figure 8:
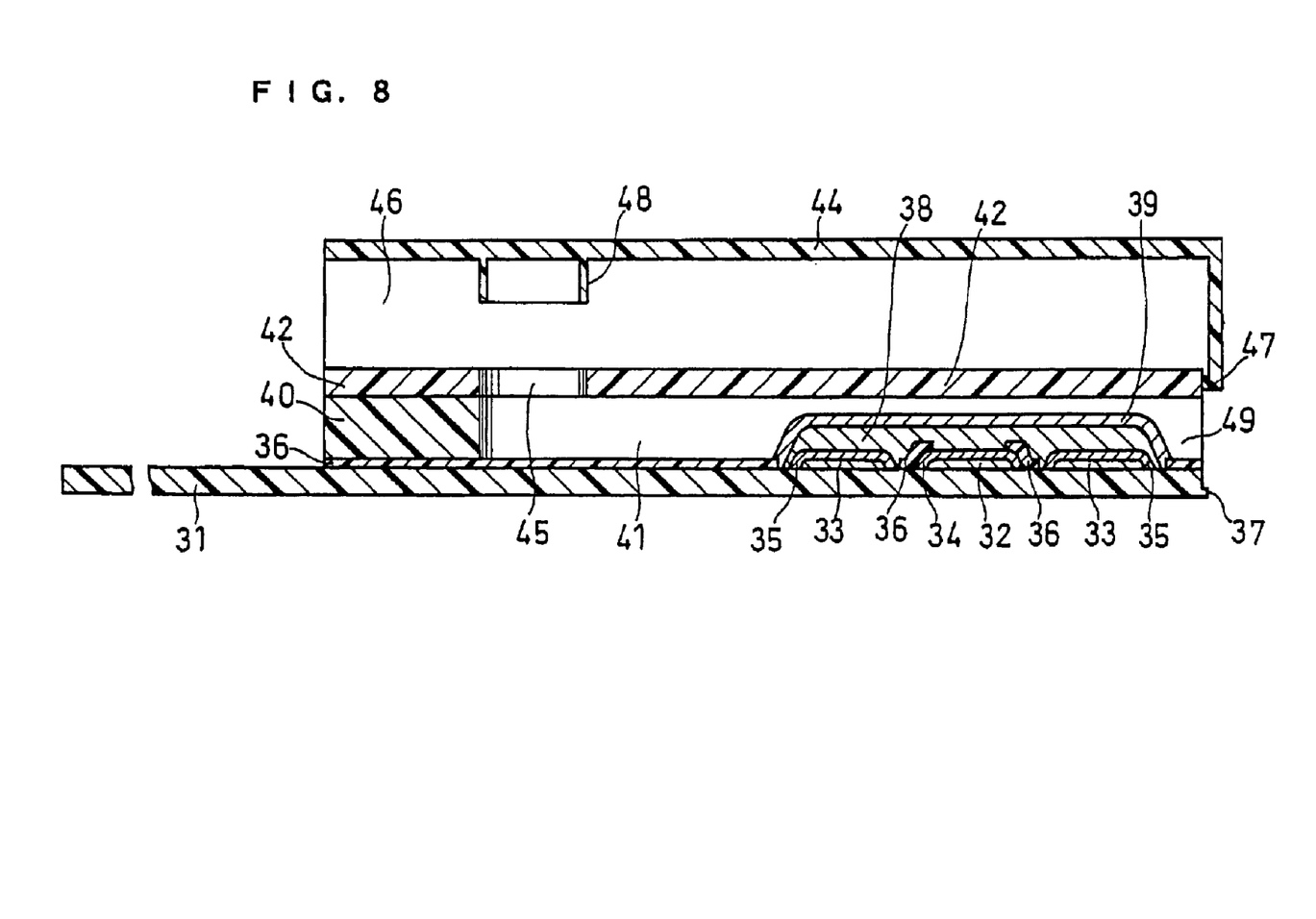
FIG. 8 is a longitudinal cross-sectional view of an analytical element in accordance with still another embodiment of the present invention.

An analytical element of this example will be described with reference to FIG. 8 and FIG. 9. FIG. 8 is a longitudinal cross-sectional view of the analytical element of this example, and FIG. 9 is an exploded perspective view of the same analytical element from which the reagent layer and surfactant layer are omitted.

First, a silver paste is printed on an electrically insulating base plate 31 made of polyethylene terephthalate by screen printing to form a working electrode lead 32 and a counter electrode lead 33. Then, a conductive carbon paste containing a resin binder is printed on the base plate 31 to form a working electrode 34. The working electrode 34 is in contact with the working electrode lead 32. Further, an insulating paste is printed on the base plate 31 to form an insulating layer 36. The insulating layer 36 covers the outer periphery of the working electrode 34 so as to keep the exposed area of the working electrode 34 constant. Thereafter, a conductive carbon paste containing a resin binder is printed on the base plate 31 so as to be in contact with the counter electrode lead 33, thereby to form a counter electrode 35.

An aqueous solution containing GOD as the oxidoreductase and potassium ferricyanide as the electron mediator is dropped over the working electrode 34 and the counter electrode 35 and is then dried to form a reagent layer 38. Over the reagent layer 38 is further formed a surfactant layer 39 containing lecithin as the surfactant.

Figure 9:
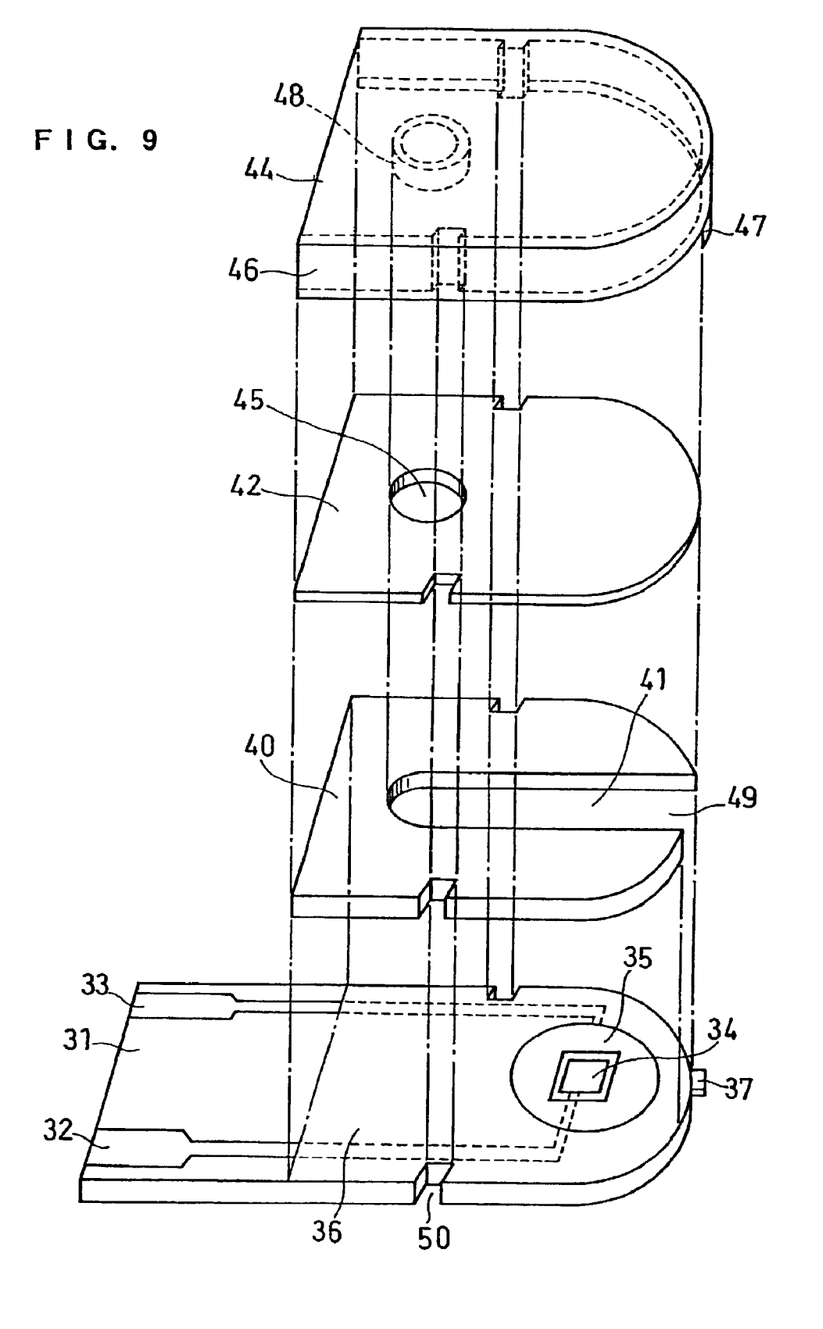
FIG. 9 is an exploded perspective view of the same analytical element from which the reagent layer and surfactant layer are omitted.

Thereafter, the base plate 31, a mid cover 42 having an air vent 45, and a spacer member 40 are bonded to one another in a positional relationship as shown by the dashed lines in FIG. 9.

The spacer member 40 to be interposed between the base plate 31 and the mid cover 42 has a slit 41, and the slit 41 forms a sample supply pathway between the base plate 31 and the mid cover 42. The air vent 45 of the mid cover 42 communicates with the sample supply pathway; thus, when a sample is brought in contact with a sample supply port 49 formed at an open end of the slit 41, the sample readily reaches the surfactant layer 39 and the reagent layer 38 in the sample supply pathway by capillary action.

Finally, a top cover 44 is mounted. The top cover 44 has a suspended part 46 which hangs down at its circumference excluding the rear end. The suspended part 46 has a protruding piece 47 which is to engage with a protruding piece 37 formed on the base plate 31 and protrusions which are to fit into indentations 50 formed in the base plate. The top cover 44 further has a cylindrical part 48 which is to fit into the air vent 45 of the mid cover 42. Thus, the top cover 44 is capable of moving perpendicularly to the electrode-printed surface of the assembly of the base plate 31, the spacer member 40 and the mid cover 42.

Using an analytical element having the above-described structure, measurements were performed for the glucose concentration of sample solutions containing certain amounts of glucose. While the top cover 44 was moved upward and held as shown in FIG. 8, a sample was supplied from the sample supply port 49 to the sample supply pathway, and thereafter, the top cover 44 was slid downward to close the sample supply port 49 and the air vent 45. At this time, the protruding piece 47 of the top cover 44 was engaged with the protruding piece 37 of the base plate 31 to fix the top cover 44 to the base plate. This prevents the top cover 44 from moving during the measurement. Then, after a lapse of certain time, a voltage of 500 mV was applied to the working electrode 34 with respect to the counter electrode 35. After the voltage application, the value of the current flowing between the working electrode 34 and the counter electrode 35 was detected, and the current response observed was proportional to the glucose concentration of the sample. At the humidities of 30% and 100%, measurements were performed with and without the sample supply port 49 and the air vent 45 covered by the top cover, and the results obtained were similar to those of Example 1.

EXAMPLE 3

Figure 10:
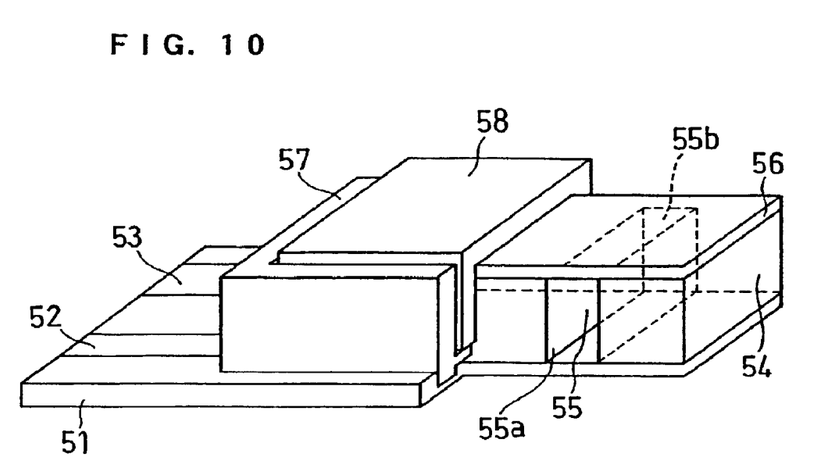
FIG. 10 is a perspective view of an analytical element in accordance with still another embodiment of the present invention.

FIG. 10 is a perspective view of an analytical element used in this example.

The analytical element of this example is composed of a base plate 51 having the same constitution as that of the base plate 31 of Example 2, a spacer 54, a mid cover 56 covering the spacer, a top cover 58, and a stopper 57. The spacer 54 has an depression 55 which is open at its both sides and bottom face, and the depression forms a cavity for accommodating a sample in combination with the base plate 51. The depression 55 of the spacer has openings 55a and 55b at its sides, and one of the openings serves as the sample supply port and the other serves as the air vent. The base plate 51 has a working electrode and a counter electrode connected to leads 52 and 53, respectively. These electrodes are exposed to the depression 55 of the spacer 54. The top cover 58 moves in parallel with the electrode-printed surface of the base plate 51 along grooves formed in the stopper 57.

After a sample is supplied from the opening 55a or 55b to the depression 55, the top cover 58 is slid to close the openings at both sides of the depression 55, and this can prevent evaporation of the sample solution. In this way, in the analytical element of this example, the similar effects to those of Example 1 can also be obtained. Further, since the top cover 58 is hidden in the stopper 57, it is possible to obtain the effect of preventing a sample such as blood from adhering to an outer surface of the top cover 58.

Examples 2 and 3 have described a constitution that the electrode system is arranged on the base plate, i.e., on the same plane, but this is not to be construed as limiting the constitution. For example, a constitution of an opposed-type electrode system such as a constitution that the electrodes are arranged so as to face each other may also be employed. Taking FIG. 8 as an example for explanation, the working electrode may be arranged on the base plate 31 and the counter electrode may be arranged on the underside of the mid cover 42.

Also, the shape of the top cover is not limited to the shape as shown in the figure and may be any shape capable of producing the effect of closing the sample supply port and air vent.

EXAMPLE 4

Figure 11:
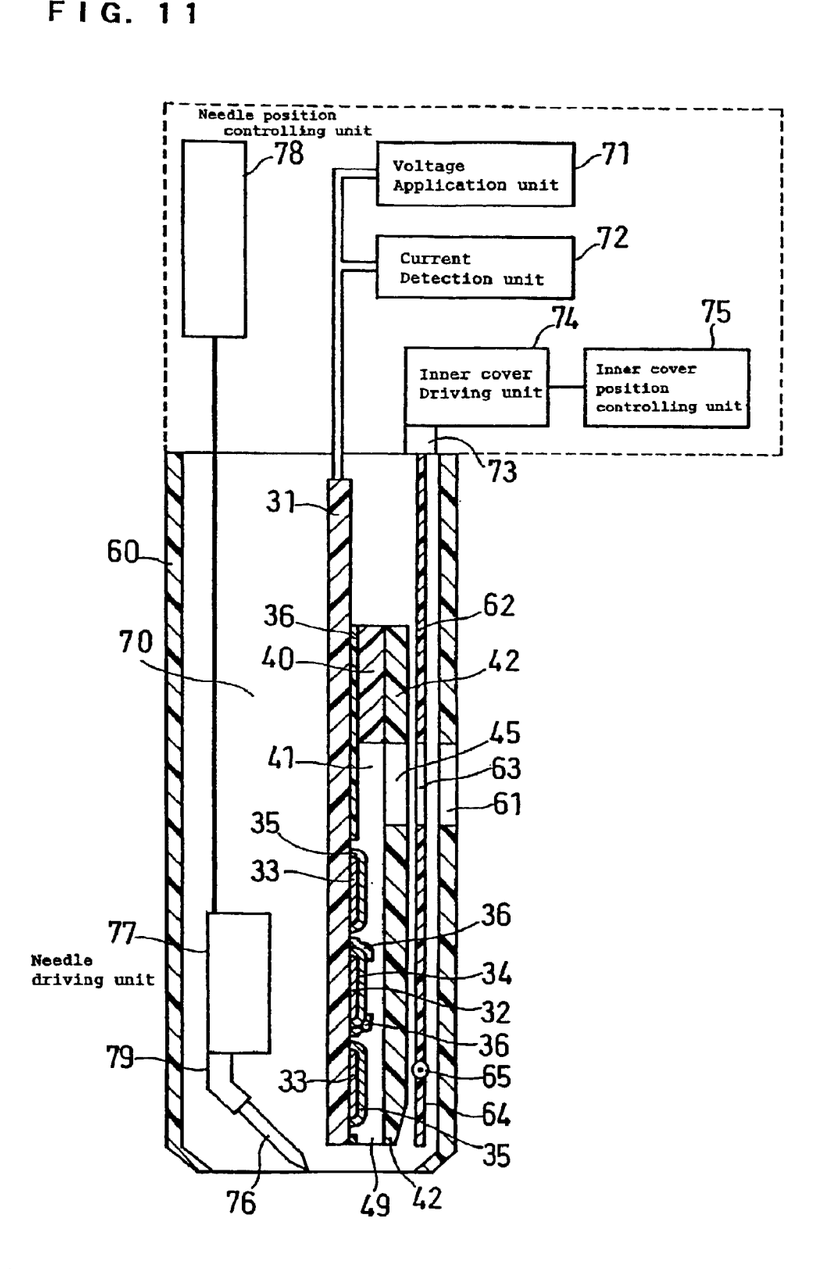
FIG. 11 is a schematic view showing the constitution of an analytical element and a measuring device in accordance with still another embodiment of the present invention.

This example will be described with reference to FIG. 11. FIG. 11 is a schematic view showing the constitution of an analytical element and a measuring device used in this example.

The analytical element 70 of this example has the same structure as that of the analytical element used in Example 2 except for the absence of the top cover which is a member covering the opening. The measuring device comprises a voltage application unit 71, a current detection unit 72, a needle 76 detachably mounted to a holder 79, a needle driving unit 77, a needle position controlling unit 78, a first inner cover 62, a connecting part 73 for connecting the inner cover 62 to an inner cover driving unit 74, a second inner cover 64 pivotally mounted to the tip end of the first inner cover 62, the inner cover driving unit 74, an inner cover position controlling unit 75, and an outer cover 60. When used for measurement, the analytical element 70 is mounted to the measuring device and fixed inside the outer cover 60 as shown in FIG. 11.

The first inner cover 62 and the outer cover 60 of the measuring device have an air vent 63 and an air vent 61, respectively, at a position facing the air vent 45 of the analytical element when the analytical element 70 is mounted to the measuring device. The second inner cover 64 can bend with a pivotal joint 65 with the first inner cover 62 as the pivot.

Next, the movement of the inner cover, which is a member covering the opening, will be described.

After a sample is introduced into the analytical element 70, the first inner cover 62 and the second inner cover 64 are pushed toward the opening of the outer cover 60. At this time, the second inner cover 64 comes in contact with the opening edge of the outer cover 60 which extends inward. Thus, the second inner cover 64 bends at the pivotal joint 65 so as to cover the sample supply port 49 of the analytical element 70. At the same time, the first inner cover 62 blocks the air vent 45 of the analytical element 70 and the air vent 61 of the outer cover 60. In this way, since the sample supply port 49 and the air vent 45 of the analytical element are substantially blocked by the inner cover mounted to the measuring device, it is possible to prevent evaporation of the sample during the measurement. Also, since the inner cover consisting of the first inner cover 62, the pivotal joint 65 and the second inner cover 64 is detachable and can therefore be cleaned easily, it is possible to provide a hygienic measuring device. Further, since the needle 76 for taking a sample is mounted inside the measuring device, an extremely small amount of sample can be introduced into the analytical element in a reliable manner; furthermore, since the inner cover prevents evaporation of the sample, reduction of the sample is possible.

FIG. 11 is just an example, and it is also possible to employ a constitution that the needle, holder, needle driving unit and needle position controlling unit are not included in the measuring device. Also, the position of the air vents 63 and 61 is not limited to the position as shown in FIG. 11 and may be adjusted appropriately depending on the shape of the analytical element.

In the foregoing examples, a voltage of 500 mV was applied to the working electrode, but this is not to be construed as limiting the voltage.

Further, the position of the air vent in the analytical element is not limited to the position as shown in the figure and may be any position if the air vent communicates with the cavity for accommodating the sample and is opposite the sample supply port side of the cavity.

Furthermore, in the foregoing examples, a solution containing an oxidoreductase was applied and dried to form the reagent layer; however, there is no limitation thereto, and a solution containing a reagent may be applied into the cavity by an ink jet method, for example. This enables precise position control in application of a very small amount of sample. Also, a solution containing a reagent may be impregnated into a glass filter paper and dried so as to cause the glass filter paper to carry the reagent, and the resultant paper may be placed into the cavity. The position of the reagent carried is preferably on the electrode, but this is not to be construed as limiting the position, and the reagent may be positioned at other parts of the cavity than the electrode if it is capable of coming in contact with the sample.

In order to form the working electrode, the counter electrode, and their leads, it is possible in the present invention to employ a method in which a conductive material in the form of a wire, foil or the like is molded with an insulating synthetic resin, a method in which a conductive paste is printed on an insulating supporting material, and a method in which a conductive layer is formed on an insulating supporting material by sputtering and is divided into a working electrode and a counter electrode by laser trimming or the like.

As the base plate for supporting the working electrode and the counter electrode, it is possible to use any electrically insulating material having sufficient rigidity during storage and measurement. Such examples include thermoplastic resins, such as polyethylene, polystyrene, poly vinyl chloride, polyamide and saturated polyester resin, or thermosetting resins, such as urea resin, melamine resin, phenol resin, epoxy resin and unsaturated polyester resin. Among them, polyethylene terephthalate is preferable in terms of the adhesion to the electrode.

As the spacer member, mid cover and top cover, it is possible to use any electrically insulating material having sufficient rigidity during storage and measurement. Such examples include thermoplastic resins, such as polyethylene, polystyrene, poly vinyl chloride, polyamide and saturated polyester resin, or thermosetting resins, such as urea resin, melamine resin, phenol resin, epoxy resin and unsaturated polyester resin.

An elastic material such as an O-ring may be preferably provided at a contacting portion of the member covering the opening with the analytical element, so that the adhesion of the member covering the opening to the analytical element is enhanced to improve the effect of preventing the evaporation of the sample.

Examples of the electron mediator include potassium ferricyanide, p-benzoquinone, phenazine methosulfate, methylene blue, and ferrocene derivatives. Also, even when oxygen is used as the electron mediator, current response is obtained. These electron mediators are used singly or in combination of two or more.

INDUSTRIAL APPLICABILITY

As described above, the present invention can provide an analytical element which can prevent evaporation of a sample during measurement and therefore quantify a substrate using a very small amount of sample with high accuracy and which can prevent scattering of the sample during and after the measurement and is therefore hygienically excellent; and a measuring device and a substrate quantification method using this analytical element.

What is claimed is:

1. An analytical element comprising a cavity for accommodating a sample, a working electrode and a counter electrode exposed to an inside of said cavity, a reagent layer which comprises at least an oxidoreductase and is formed inside or in the vicinity of said cavity, an opening communicating with said cavity and a member for covering said opening, and a driving unit coupled to the member, wherein the driving unit drives the member to cover and/or uncover the opening.

2. The analytical element in accordance with claim 1, wherein the member covering the opening is a puncture member.

3. The analytical element in accordance with claim 1, wherein the member covering the opening is transparent.

4. The analytical element in accordance with claim 1, wherein the member covering the opening also serves as the working electrode or the counter electrode.

5. The analytical element in accordance with one of claims 1 though 4, wherein the member covering the opening is provided with the reagent layer.

6. The analytical element in accordance with claim 1, further comprising a position controlling unit coupled to the driving unit, said position controlling unit controlling the position of said member.

7. An analytical element comprising: a rod-like element body comprising an insulating member which has a depression for accommodating a sample at its side face in the vicinity of its tip end and a working electrode and a counter electrode arranged so as to be exposed to an inside of said depression; a cover which covers the face of the element body having said depression, said cover having a groove along a longitudinal direction of said element body at a portion facing said depression; a reagent layer which comprises at least an oxidoreductase and is formed inside or in the vicinity of said depression; and a puncture member which moves in the longitudinal direction of the element body in said groove and sticks out of the tip end of the element body to puncture a subject, wherein a sample supply opening communicating with said depression is formed between the tip end of the element body and the cover, an air vent is formed at or above a position of the cover corresponding to said depression, and the puncture member is capable of substantially covering said depression.

8. An analytical element comprising: an element body comprising an insulating base plate on which an electrode system comprising a working electrode and a counter electrode is formed and a cover member which covers said base plate and forms a sample supply pathway communicating with said electrode system between the cover and the base plate; a reagent layer which comprises at least an oxidoreductase and is formed inside said sample supply pathway; and a top cover, wherein said sample supply pathway extends from a sample supply port at one end of the element body to an air vent formed in the cover member, and the top cover is configured so as to be combined to the element body by sliding it in a direction perpendicular to the element body such that it closes said sample supply port and the air vent when it is in close contact with the element body.

9. A measuring device comprising: an analytical element comprising a cavity for accommodating a sample, a working electrode and a counter electrode exposed to an inside of said cavity, a reagent layer which comprises at least an oxidoreductase and is formed inside or in the vicinity of said cavity, an opening communicating with said cavity and a member for covering said opening, and a driving unit coupled to the member, wherein the driving unit drives the member to cover and/or uncover the opening; voltage application means for applying a voltage between said working electrode and said counter electrode; and signal detecting means for detecting an electric signal between said working electrode and said counter electrode upon voltage application, wherein the amount of reaction between a substrate contained in the sample and said oxidoreductase is electrochemically detected to quantify said substrate.

10. The measuring device in accordance with claim 9, wherein the member of the analytical element covering the opening is detachable.

11. The measuring device in accordance with claim 9, wherein said analytical element further comprises a position controlling unit coupled to the driving unit, said position controlling unit controlling the position of said member.

12. A substrate quantification method comprising the steps of:

preparing an analytical element comprising a cavity for accommodating a sample, a working electrode and a counter electrode exposed to an inside of said cavity, a reagent layer which comprises at least an oxidoreductase and is formed inside or in the vicinity of said cavity, an opening communicating with said cavity and a member for selectively covering said opening, and a driving unit coupled to the member, wherein the driving unit drives the member to cover and/or uncover the opening;

supplying the sample to said analytical element to react a substrate contained in the sample with said oxidoreductase;

closing said opening;

applying a voltage between said working electrode and said counter electrode; and detecting a change in electric signal between said working electrode and said counter electrode upon said voltage application.

13. The substrate quantification method in accordance with claim 12, wherein said analytical element further comprises a position controlling unit coupled to the driving unit, said position controlling unit controlling the position of said member.

14. An analytical element comprising a cavity for accommodating a sample, a working electrode and a counter electrode exposed to an inside of said cavity, a reagent layer which comprises at least an oxidoreductase and is formed inside or in the vicinity of said cavity, an opening communicating with said cavity and a member covering said opening, wherein the member covering the opening is a puncture member.

15. The analytical element in accordance with claim 14, wherein the member covering the opening is transparent.

16. The analytical element in accordance with claim 14, wherein the member covering the opening also serves as the working electrode or the counter electrode.

17. The analytical element in accordance with claim 14, wherein the member covering the opening is provided with the reagent layer.

18. An analytical element comprising a cavity for accommodating a sample, a working electrode and a counter electrode exposed to an inside of said cavity, a reagent layer which comprises at least an oxidoreductase and is formed inside or in the vicinity of said cavity, an opening communicating with said cavity and a member covering said opening, wherein the member covering the opening also serves as the working electrode or the counter electrode.

19. The analytical element in accordance with claim 18, wherein the member covering the opening is provided with the reagent layer.

20. An analytical element comprising a cavity for accommodating a sample, a working electrode and a counter electrode exposed to an inside of said cavity, a reagent layer which comprises at least an oxidoreductase and is formed inside or in the vicinity of said cavity, an opening communicating with said cavity and a member covering said opening, wherein the member covering the opening is provided with the reagent layer.

* * * * *

UNITED STATES PATENT AND TRADEMARK OFFICE
CERTIFICATE OF CORRECTION

PATENT NO. : 6,878,262 B2
DATED : April 12, 2005
INVENTOR(S) : Yuko Taniike et al.

It is certified that error appears in the above-identified patent and that said Letters Patent is hereby corrected as shown below:

<u>Column 13,</u>
Line 66, change "1 though 4" to -- 1 through 4 --.

Signed and Sealed this

Twentieth Day of September, 2005

JON W. DUDAS
*Director of the United States Patent and Trademark Office*